(12) United States Patent
Lagarde

(10) Patent No.: US 7,115,090 B2
(45) Date of Patent: Oct. 3, 2006

(54) METHOD AND DEVICE FOR PRETREATMENT OF SAMPLES BY CENTRIFUGING

(75) Inventor: Benoit Lagarde, Sannois (FR)

(73) Assignee: Stago Instruments, Gennevilliers (FR)

( * ) Notice: Subject to any disclaimer, the term of this patent is extended or adjusted under 35 U.S.C. 154(b) by 68 days.

(21) Appl. No.: 10/523,073

(22) PCT Filed: Jul. 4, 2003

(86) PCT No.: PCT/FR03/02094

§ 371 (c)(1),
(2), (4) Date: Jan. 25, 2005

(87) PCT Pub. No.: WO2004/011152

PCT Pub. Date: Feb. 5, 2004

(65) Prior Publication Data

US 2006/0116269 A1 Jun. 1, 2006

(30) Foreign Application Priority Data

Jul. 25, 2002 (FR) .................................. 02 09626

(51) Int. Cl.
*B04B 13/00* (2006.01)
*B04B 9/14* (2006.01)
*B04B 5/02* (2006.01)
*G01N 35/04* (2006.01)

(52) U.S. Cl. ............................ 494/10; 494/20; 494/82; 74/572.4; 422/72

(58) Field of Classification Search .................. 494/1, 494/10, 12, 20, 33, 82, 84; 422/72; 210/85, 210/144; 68/23.1, 23.2; 73/457, 458; 74/572.4
See application file for complete search history.

(56) References Cited

U.S. PATENT DOCUMENTS

| 5,538,493 | A | * | 7/1996 | Gerken et al. ............... 494/16 |
| 5,730,697 | A | * | 3/1998 | Auchinleck .................. 494/20 |
| 5,769,775 | A | | 6/1998 | Quinlan et al. |
| 6,060,022 | A | | 5/2000 | Pang et al. |
| 6,196,961 | B1 | * | 3/2001 | Hoshiba et al. .............. 494/14 |
| 6,758,803 | B1 | * | 7/2004 | Jang ............................ 494/10 |
| 6,949,063 | B1 | * | 9/2005 | Baik et al. .................... 494/1 |
| 7,025,714 | B1 | * | 4/2006 | Escal ............................ 494/1 |
| 2002/0132354 | A1 | * | 9/2002 | Downs et al. ................ 436/45 |

FOREIGN PATENT DOCUMENTS

| EP | 1 003 020 A | | 5/2000 |
| FR | 2842912 | * | 1/2004 |
| JP | 07 080355 A | | 3/1995 |
| JP | 7-234229 | * | 9/1995 |
| JP | 09 276743 A | | 10/1997 |
| JP | 11-262682 | * | 9/1999 |
| WO | 2006/033502 A1 | * | 3/2006 |

* cited by examiner

Primary Examiner—Charles E. Cooley
(74) Attorney, Agent, or Firm—Browdy and Neimark, PLLC

(57) ABSTRACT

The invention concerns a method comprising detecting tubes inside carriers (P), detecting an expected imbalance of the centrifuge (CE) and, when said detection reveals the presence of such an imbalance owing to the presence of an insufficient number of carriers (P) or an odd number of carriers (P), the method consists in: simulating the load of the centrifuge incorporating the incomplete carrier (P), selecting a balance-restoring carrier based on the number of tubes missing in the incomplete carrier (P), determining the boat of the centrifuge (CE) wherein the balancing carrier should be placed and installing said carrier in the boat.

10 Claims, 5 Drawing Sheets

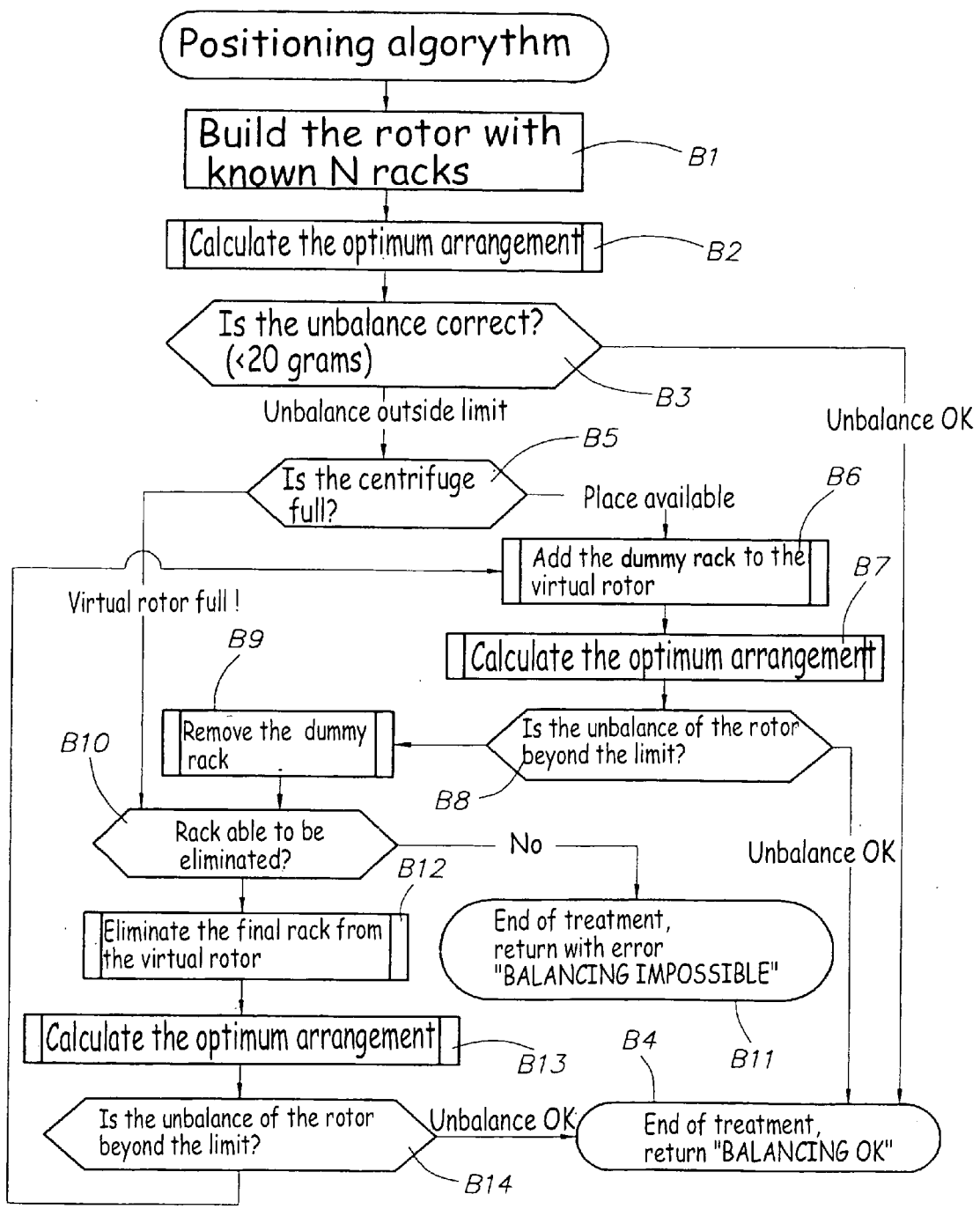

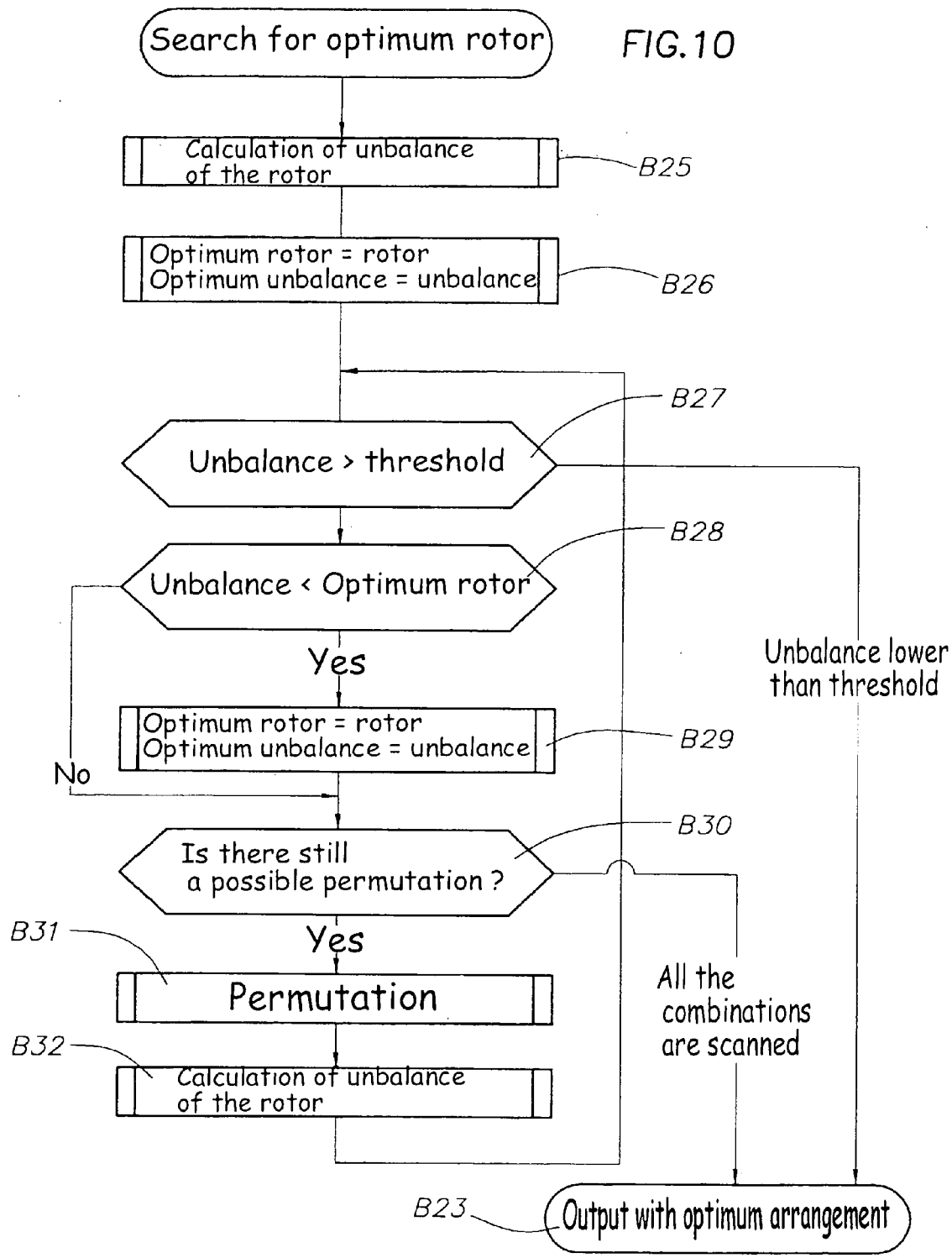

METHOD AND DEVICE FOR PRETREATMENT OF SAMPLES BY CENTRIFUGING

The present invention concerns a method and a device for pretreating via the centrifuging of blood samples contained in tubes prior to being introduced into an automatic analysis device.

Generally speaking, so as to analyse them, the tubes of samples are normally arranged in lines inside containers or sample racks, each containing several tubes (usually five) axed vertically in a longitudinal vertical median plane of the container.

These containers include a base in which a transversal prismatic cavity is made having a T-shaped section (or round tail).

They are transported inside baskets whose bottoms are equipped with rails having profiles complementary to that of said cavities.

They are introduced into these baskets by being placed side by side so as to form a line orientated perpendicular to their longitudinal axis and by moving them in translation in the direction of the line so as to have them slide inside the baskets where they are supported and guided by maen of the engaging of the rail in the cavities of the containers.

The transfer of the containers of the baskets where they are located to the analysis robot is carried out by means of a mobile thrustor in the axis of the rail and whose step by step movements are ensured by a mechanism comprising a backgeared motor which drives a pinion which gears with a rack axed perpendicularly to the rail and on which the thrustor is rendered integral.

This thrustor is able to move the containers along the rail so as to bring the final container of the line onto a belt conveyor axed perpendicular to the rail which feeds the analysis robot.

In the case where it is desired to carry out certain types of analysis, such as hemostasis tests on blood samples, it is necessary to centrifuge these samples before conducting analysis in the analysis robot.

To this effect, centrifugal machines are used including a rotor with an axis of vertical rotation to the periphery from which a plurality of boats are mounted tilting and able to each contain one or several containers of tubes of samples.

Once the containers are placed in the boat (in a vertical position), the rotor is driven in rotation. Because of this, under the effect of the centrifugal force, the boats are placed horizontally and the samplings contained in the tubes undergo a centrifuging.

Of course, this centrifuging process can only be carried out if the unit constituted by the rotor, the boats and the containers provided with their tubes is correctly balanced.

In fact, if this unit is not correctly balanced, its rotation generates a vibratory moment which is no longer able to be tolerated beyond a specific threshold.

Owing to this, the centrifugal machine comprises a safety system which stops the centrifugal machine when this vibratory moment exceeds said threshold.

So as to take account of this problem, it is therefore necessary to provide prior to each centrifuging stage a balancing stage.

This stage can be carried out manually by adding test tubes in the incomplete containers. However, this solution involves the continuous presence of an operator at the centrifuging station. In fact, this balancing stage is difficult to make automatic and usually involves access to the containers already placed in the boats of the centrifugal machine which makes it necessary to intervene concerning the design of the centrifugal machine.

Thus, the object of the invention is to provide a centrifuging device in which feeding the centrifugal machine with containers, the balancing of the centrifugal machine and the transfer of the containers from the centrifugal machine to the analysis robot are carried out automatically with the aid of relatively simple reliable and inexpensive elements.

To this effect, the invention provides a method including the following operational phases:

the detection of the presence of tubes inside the containers at the time the latter are transported to the centrifugal machine;

the detection of a foreseeable lack of balance of the centrifugal machine and when this detection reveals to the presence of this lack of balance due to the presence of an incomplete container;

the simulation of the load of the centrifugal machine incorporating the incomplete container;

the selection of a balancing container according to the number of tubes missing in the incomplete container or an odd number of containers;

the determination of the boat of the centrifugal machine inside which the balancing container needs to be placed so as to obtain a good balancing of the load;

the placing of this container in said boat in the place of the samples container which should to be already there, thus provoking a shift in the order for introducing the sample containers in the centrifugal machine;

the replacing of the balancing container onto its storage area during the transfer of the sampling containers to the robot once centrifuging has been carried out.

As regards the selection of the balancing containers, the invention simplifies this operation by being based on the fact that the centrifugal machine tolerates a lack of balance slightly exceeding the lack of balance brought about by the absence of one tube out of five normally present in the container. Because of this, it is enough to provide only two types of balancing containers respectively corresponding to one container containing two tubes and one container containing four tubes so as to compensate all the possible lacks of balance.

One embodiment of the invention is described hereafter and is given by way of non-restrictive example with reference to the accompanying drawings on which:

FIGS. 9 and 10 are flow charts of the programme used to balance the centrifugal machine.

Figure 1:
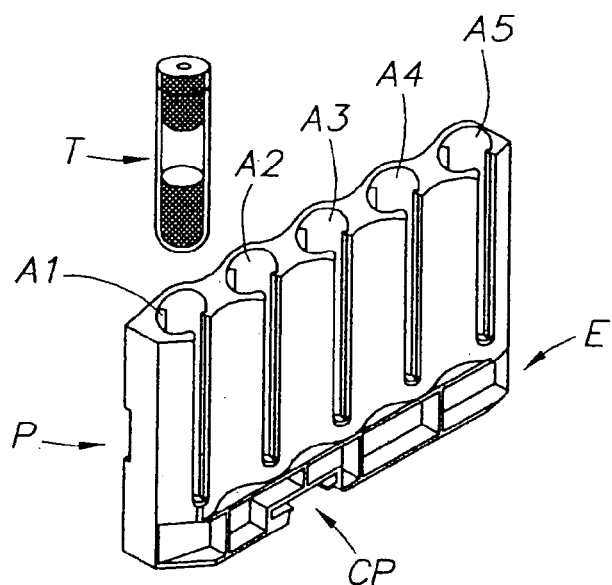
FIG. 1 is a diagrammatic perspective view of a tube container.

In this example, the device of the invention is intended to pretreat by means of centrifuging the samples contained in tubes T placed in containers P, such as the one shown on FIG. 1 prior to the introduction of these containers P one by one into an analysis robot AA.

This analysis robot AA may comprise, as described in the patent FR No 97 07 751 filed in the name of the Applicant, a pipetting area in which the tubes of samples T, placed in their containers P and previously identified, are successively brought and above which a pipette head moves.

Figure 2:
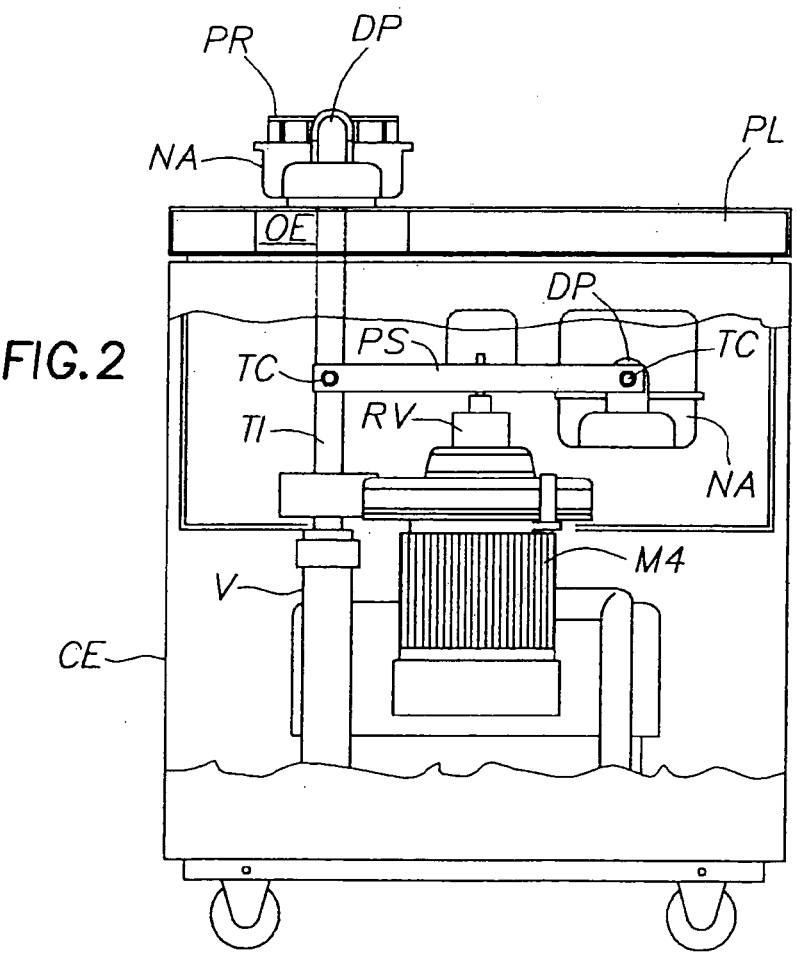
FIG. 2 is a diagrammatic vertical section of a centrifugal machine.

During the process preceding the phase for carrying out tests in the analysis robot AA, the containers P containing the tubes (sealed) of samples (for example blood samples) are placed in the boats NA of a centrifugal machine CE, such as the one illustrated on FIG. 2 where they are subjected to centrifuging. Throughout this process, the tubes T are kept inside the containers so as to avoid being handled.

On leaving the centrifugal machine CE, the containers containing the tubes are brought into specially designed baskets placed in a container distributor $DP_1$ which equips the feeding station $PA_1$ of the containers P at the analysis robot AA.

The containers P used may consist of the container P shown on FIG. 1 and having a general parallelepiped shape with bevelled vertical edges. This container comprises a base E provided with a ribbing delimiting a transversal prismatic cavity CP having an approximately C-shaped section or round tail and intended to cooperate with a guiding rail RG having a complementary T-shaped section.

This rail RG is provided at the bottom of the baskets $PA_1$, $PA_2$ and in the transfer areas in which the containers P are moved in translation perpendicular to their axis of symmetry.

The upper portion of the container P here comprises five vertical cylindrical alveoles $A_1$ to $A_5$ opened at the level of the upper face of the container and intended to receive five respective tubes T.

FIGS. 3 to 7 show the path followed by the containers P in the pretreating device from a station $PA_2$ for feeding this device in which the containers P are placed in baskets as far as the feeding station of the analysis robot where these containers are again brought together in a basket $PA_1$ associated with a one-by-one container distributor $DP_1$.

In these figures, the centrifugal machine CE has been shown in the shape of a rectangular block inside which an extraction feeding area AL is also represented by a block in which the containers can be successively introduced or extracted by means of a grasping mechanism MP.

The feeding station $PA_2$ is placed along one lateral side $CL_1$ of the centrifugal machine CE situated opposite the feeding station $PA_1$ of the robot AA, these two stations $PA_1$, $PA_2$ being approximately adjacent to the front side CA of the centrifugal machine CE.

It is equipped with a mobile thrustor $PM_1$ in translation along the lateral side $CL_1$ and driven by a device introducing a motor $M_1$ which drives a pinion geared onto a rack $CR_1$.

The purpose of this thrustor $PM_1$ is to extract the containers P contained in the baskets situated in the feed station $PA_1$, to bring them into a storage area $AS_1$ adjacent to a belt conveyor BT driven by a motor $M_2$ which runs parallel to the rear side CP of the centrifugal machine CE and thus perpendicular to the displacement axis of the thrustor $PM_1$.

This belt conveyor BT transports one by one the containers P pushed by the thrustor $PM_1$ to a grasping area in which the grasping mechanism MP takes them so as to bring them to the feeding area AL of the centrifugal machine CE where they are placed in the boats NA. The belt conveyor BT further allows the transportation of the thrustors P extracted from the centrifugal machine CE by the grasping means to a transport area situated on the lateral side $CL_2$ of the centrifugal machine CE adjacent to the feeding station $PA_2$ of the robot AA. This transport area introduces a thrustor $PM_2$ able to move perpendicular to the direction of running off of the belt conveyor BT so as to transfer via a translation movement the containers P brought by the belt conveyor BT into the basket equipping the feeding station $PA_1$. To this effect, the thrustor $PM_2$ is activated by means of a mechanism introducing a gear driven in rotation by a motor $M_3$ which gears with a rack $CR_2$.

The distribution of the containers P contained in the basket of the feeding station $PA_1$ inside the analysis robot AA is effected with the aid of an endless belt CS mounted on rollers axed vertically, one of said rollers being driven in rotation by a motor. This belt CS, placed at the end of the basket parallel to the containers P, bears a drive dog able to be geared on the extremity of the containers P and situated opposite the intake opening of the analysis robot AA.

Figure 3:
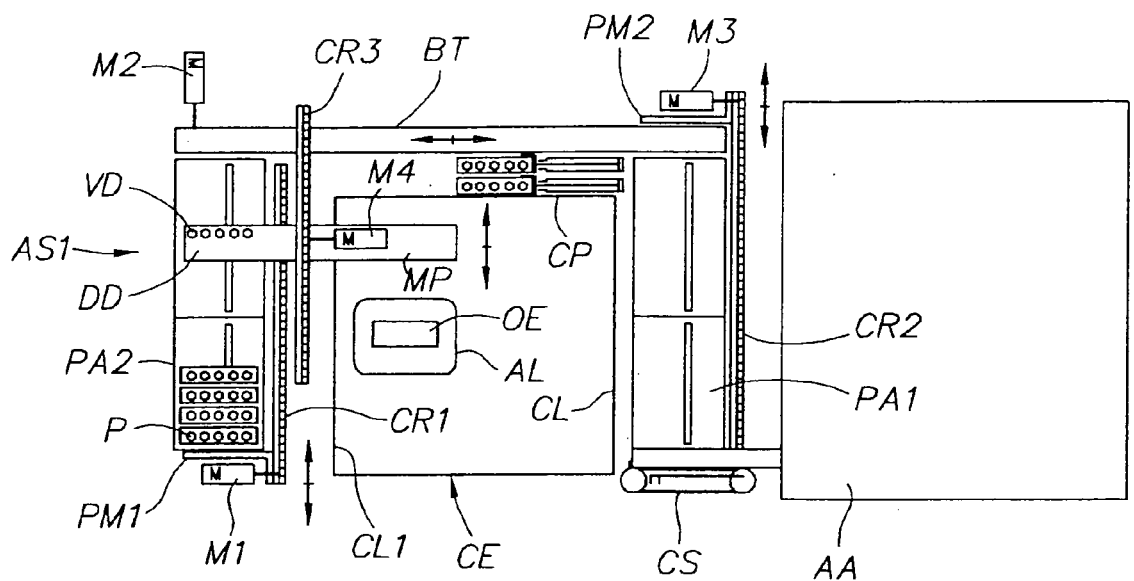
FIGS. 3 to 6 are top views of a centrifuging device according to the invention at various stages for the functioning of said device.

As shown on FIG. 3, the centrifugal machine CE could advantageously include a rotor RV with a vertical axis driven by an electric motor $M_4$ and comprising a rotary support element PS provided with a plurality of pairs of coaxial journals TC on each of which it is possible to suspend oscillating boats NA designed to receive the containers P at the rate of one or several containers per boat. In this example, the means to ensure suspension and allow rotation of the boats NA consists of half bearing DP open towards the bottom in which the journals TC are engaged so that these boats NA can be easily extracted by lifting them up.

The whole of this mechanism is housed inside a box closed at its upper portion by a plate PL which includes at the level of said feed zone an orifice OE used for extracting the boats NA.

To this effect, the centrifugal machine includes an extraction mechanism consisting of a support element mounted on the rod T1 of a jack placed below the orifice OE and intended to lift up the boats NA up to a level situated above the plate PL so that the containers P contained in the boats NA can be picked up by the grasping means MP, or conversely these grasping means MP can be laid with new containers P.

At the time they are lifted up, the boats NA can be rendered integral temporarily on the extremity of the support element with the aid of permanent magnets.

As mentioned previously, the aim of the invention is to automatically resolve the problems of the balancing of loads of the rotor so as to obtain a fully automated functioning of centrifuging, as well as the various transfers of the containers to the feeding station of the robot.

To this effect, the invention provides a device for detecting the presence of tubes inside the containers during their path from the feeding station $PA_2$ up to the belt conveyor BT.

This detection device DD here includes a row of detection jacks VD axed perpendicular to the displacement axis of the containers P and mounted on a structure moving in translation above the containers P from the station $PA_2$ as far as the belt conveyor BT. (The detection of the presence of a tube being obtained when the rod of the jack stopped on the tube is unable to carry out a complete travel).

Driven is provided by a mechanism introducing a motor $M_4$ driving a pinion which gears on a rack $CR_3$.

The mechanism for picking up and transporting the containers between the belt conveyor BT and the feeding area AL of the centrifugal machine CE is integral with the structure bearing the detection jacks VD.

In accordance with the invention, this device introduces a processor which controls all the motors $M_1$ to $M_4$ of the belt distributor CS, as well as the functioning of the centrifugal machine so as to obtain the following operating sequence.

Initially, a basket containing the containers (in this instance four) is placed in the feeding station $PA_2$, the thrustor $PM_1$ being in a pushed back position (FIG. 3).

Figure 4:
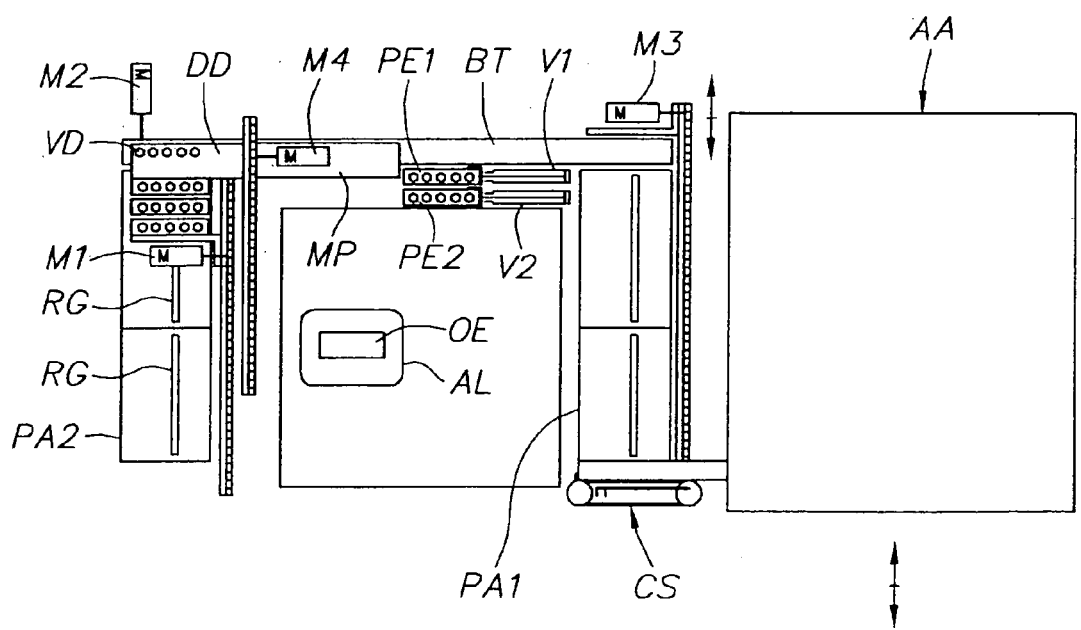

The thrustor $PM_1$ is then activated and pushes back the four containers P into a storage area adjacent to the belt conveyor BT (FIG. 4). The presence detection device DD then moves above the containers P and, for each container P, detects the presence or absence of the tubes T contained in this container P. The information relating to these presences or absences is sent to the processor.

At the end of detection, the presence detector and accordingly the grasping mechanism are arranged above the belt conveyor BT (FIG. 4).

This processor conducts simulations by means of the information originating from the device DD so as to be able to allocate each of the thrusters PM to a boat of the centrifugal machine CE so as to balance the latter. In the case where the processor observes a lack of balance, it is able to replace one of the thrusters with a balancing thrustor $PE_1$, $PE_2$.

As mentioned previously, in the case where the tolerance permitted by the centrifugal machine CE is one tube per container, it is possible to only use two different types of balancing containers $PE_1$, $PE_2$ corresponding respectively to one container including four tubes and one container including two tubes.

Figure 8:
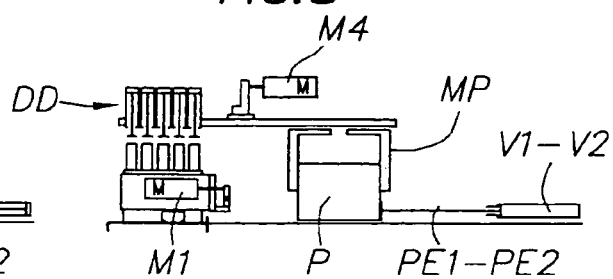

These two containers $PE_1$, $PE_2$ are placed on a storage area of the plate of the centrifugal machine and pushed by two respective jacks to a location accessible by the grasping mechanism MP (FIG. 8).

Figure 5:
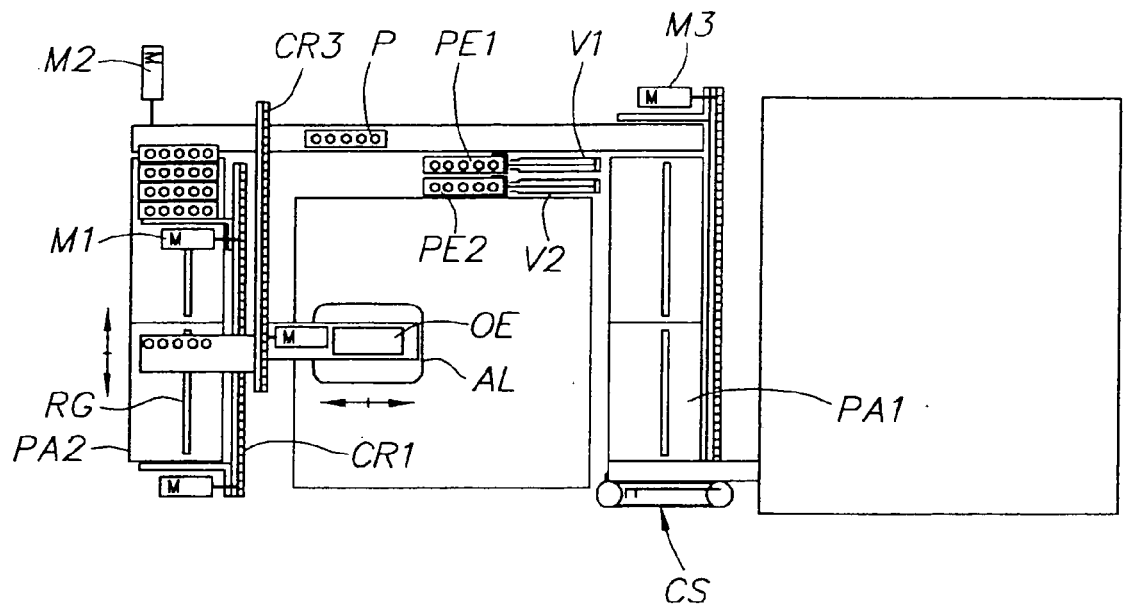
Figure 6:
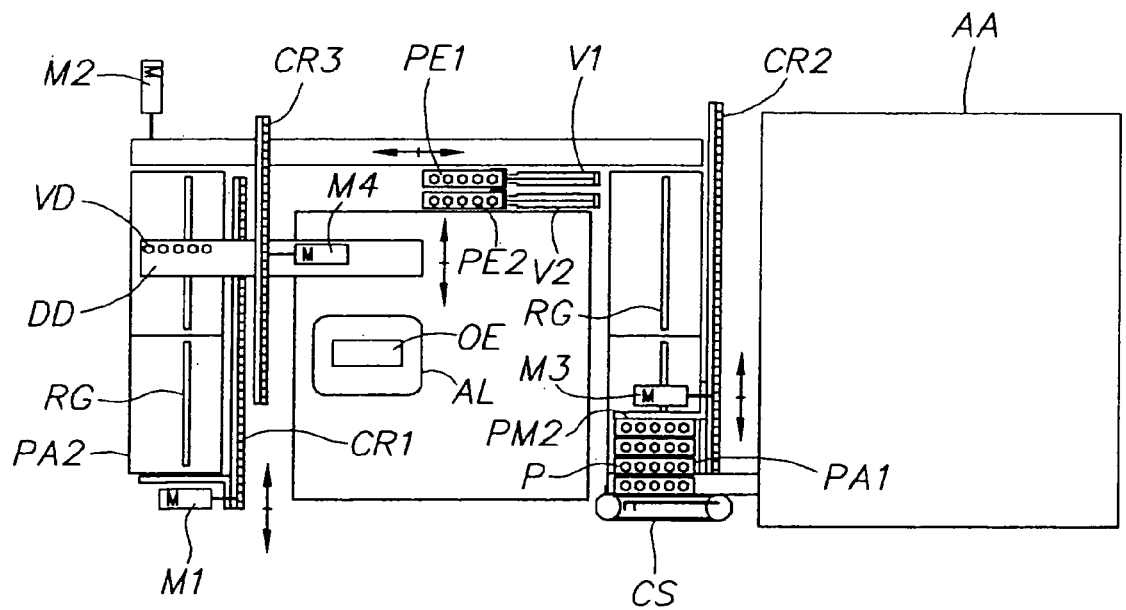
Figure 7:
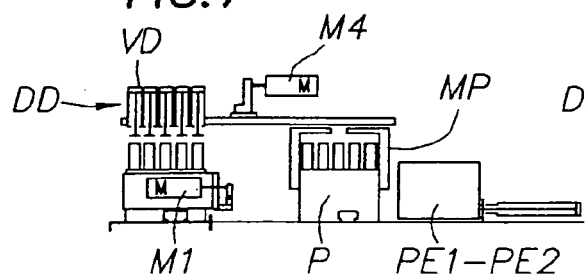
FIGS. 7 and 8 are diagrammatic axial sections illustrating the operating principle of the device for feeding the centrifugal machine associated with the detector detecting the presence of tubes in the containers.

Once the processor has allocated to each of the boats NA a container P (possibly a balancing container), the thrustor $PM_i$ pushes the containers P one by one onto the belt conveyor BT. Each container is then picked up by the grasping mechanism MP which transports it and introduces it into the boat NA located above the orifice OE (FIGS. 5 and 7).

Once a thrustor PM has been introduced into a boat NA, the boat NA is lowered again by the jack V so as to be again suspended from the journals TC of the support element PS. The rotor RV then rotates so as to bring the next boat NA determined by the processor (virtual rotor) to the right of the orifice OE. The jack V can then lift up this boat NA so as to have it pass through the orifice OE up to a position in which it is able to receive a container P which has been allocated to it by the processor.

Once all the boats NA are provided with containers P, the centrifugal machine CE carries out a centrifuging stage.

Via an inverse process, the centrifugal machine CE is unloaded. To this effect, the boats NA are successively lifted up by the jack V so as to present the container(s) P they contain at the grasping mechanism MP. This mechanism brings the container P back onto the conveyor belt BT or, when it involves a balancing container, onto the storage area.

The containers P brought back onto the belt conveyor BT are brought one by one to the right of the thrustor $PM_2$ which pushes them back onto the basket $PA_1$ situated in the feeding area of the robot AA. These containers P are then moved into the robot by the belt CS.

FIGS. 9 and 10 show the various stages carried out by the processor so as to determine the positioning of the containers inside the centrifugal machine.

So as to determine this positioning, the processor implements the positioning algorithm shown on FIG. 9 which includes first of all the construction of a virtual rotor (block $B_1$) containing the containers P in which the presence of the tubes T has been detected by the presence detectors, followed by the calculation of the optimum arrangement (block $B_2$). The processor next calculates the unbalance of this arrangement and determines if this unbalance is correct or not (for example if it is less than 20 grams) (block $B_3$).

If the unbalance is correct, the balancing treatment ends (block $B_4$).

On the other hand, if the unbalance exceeds the fixed limit (here 20 grams), the processor determines if the centrifugal machine is full (block $B_5$).

If there is a place available, the processor adds a balancing container to the virtual rotor (block $B_6$) and then it calculates the optimum arrangement (block $B_7$). If the new unbalance of the rotor is correct (less than the limit) (block $B_8$), the balancing treatment ends. (block $B_4$). If the unbalance of the rotor exceeds the limit (block $B_8$), the processor eliminates the balancing container (block $B_9$) and then determines if there is a container able to be eliminated (block $B_{10}$). If this is not the case, the processor ends the treatment and triggers an error signal signifying that balancing is impossible (block $B_{11}$). If there is a container able to be eliminated (block $B_{10}$), the processor eliminates the final container of the virtual rotor (block $B_{12}$) and calculates the optimum arrangement (block $B_{13}$).

If the unbalance of the rotor is outside the limit (block $B_{14}$), the processor returns to the stage for adding a balancing container (block $B_6$). On the other hand, if the unbalance is correct, the balancing treatment ends (block $B_4$).

If, during finding if the centrifugal machine is full (block $B_5$) the virtual rotor is full, the processor moves directly to the determination stage if there exists a container able to be eliminated (block $B_{10}$).

The stage for calculating the optimum arrangement provided on the algorithm of FIG. 9 (blocks $B_2$ and $B_7$) can be carried out in accordance with the algorithm of FIG. 10 which successively includes the calculation of the unbalance of the rotor (block $B_{25}$), the determination of the optimum rotor, as well as the optimum unbalance (block $B_{26}$).

The processor then determines if the unbalance is lower than a predetermined threshold (block $B_{27}$) and lower than the optimum unbalance (block $B_{28}$).

If the unbalance is lower than the threshold, the search for the optimum rotor ends (block $B_{28}$). If the unbalance is lower than the optimum unbalance (block $B_{28}$), the system determines the optimum rotor and the optimum unbalance (block $B_{29}$) and if there still exists a possible permutation (block $B_{30}$). If the unbalance were lower than the optimum unbalance at the block $B_{28}$, the system passes directly to the block $B_{30}$.

If no permutation is possible, this means that all the permutations have been scanned and the search for the optimum rotor ends (block $B_{28}$). If a permutation is possible, the system carries out the permutation (block $B_{31}$) and then calculates the unbalance of the rotor (bock $B_{32}$) and returns to the block $B_{27}$ for a new sequence.

The invention claimed is:

1. Method for pretreating via centrifuging samples contained in tubes-placed in containers prior to being introduced into an automatic analysis device, the centrifuging being effected in a centrifugal machine comprising a rotor with a vertical axis, a plurality of boats being mounted tilting at the periphery of said rotor, said boats being able to each contain one container with tubes of samples, said method comprising the steps of detecting the presence of tubes inside the containers at the time they are transported to the centrifugal machine, detecting a foreseeable lack of balance of the centrifugal machine and when this detection reveals the presence of this lack of balance owing to the presence of incomplete containers or an odd number of containers:

simulating the load of the centrifugal machine incorporating the incomplete container;

selecting a balancing container according to the number of tubes missing in the incomplete container;

determining the boat of the centrifugal machine inside which the balancing container needs to be arranged so as to obtain a good balancing of the load;

placing this container in said boat in the place of the samples container which would be there, thus provoking a shift in the order of the introduction of the balancing containers in the centrifugal machine;

putting back the balancing container on its storage area at the time of transferring the sample containers to the automatic analysis device once centrifuging has been carried out.

2. Method according to claim 1, wherein, in the case where the capacity of the containers is five tubes and where the centrifugal machine tolerates a lack of balance equal at least to that brought about by the absence of a tube, it only uses two balancing containers respectively corresponding to one container containing two tubes and one container containing four tubes so as to compensate all the possible lacks of balance.

3. Method according to claim 1, wherein in order to determine the positioning of the containers inside the centrifugal machine, it comprises the steps of constructing a virtual rotor containing the containers in which the presence of the tubes has been detected by presence detectors, calculating an optimum arrangement and the unbalance of this arrangement, testing to know if the unbalance is correct or not, the balancing treatment ending if the unbalance is correct, in the case where the unbalance is incorrect, determining the state (full or empty) of the centrifugal machine, if an available place exists adding a balancing container to the virtual rotor, calculating an optimum arrangement, if the new unbalance of the rotor is correct, ending the balancing treatment;

if the new unbalance is incorrect, eliminating the balancing container, testing to know if there is a container able to be eliminated, if this is not the case ending the treatment and trigerring an error signal, whereas if there is a container able to be eliminated eliminating the last container from the virtual rotor—and calculating the optimum arrangement, in the case where the unbalance of the rotor is incorrect, returning to the balancing addition step, the treatment being ended if this unbalance is correct.

4. Method according to claim 3, wherein, if during the test carried out to know if the centrifugal machine is full, the virtual rotor is full, it comprises a direct passage to the determination stage if there exists a container able to be suppressed.

5. Method according to claim 4, wherein the stage for finding an optimum rotor successively comprises the calculation of the rotor of the unbalance of the rotor, the determination of the optimum rotor and of the optimum unbalance, a test to know if the unbalance is lower than a predetermined threshold and lower than the optimum unbalance, if the unbalance is lower than said threshold, the search for the optimum rotor ends; if the unbalance is lower than the optimum unbalance, the determination is made of the optimum rotor and of the optimum unbalance and of the existence of a possible permutation, it being understood that if the unbalance is lower than the optimum unbalance the system passes directly to the step of determination of a possible permutation, the search ending if no permutation is possible, whereas if a permutation is possible the system carrying out the permutation, calculating the unbalance of the rotor and then returning to the step of testing to know if the unbalance is lower than a predetermined threshold for a new sequence.

6. Method according to claim 3, wherein the stage for finding an optimum rotor successively comprises the calculation of the rotor of the unbalance of the rotor, the determination of the optimum rotor and of the optimum unbalance, a test to know if the unbalance is lower than a predetermined threshold and lower than the optimum unbalance, if the unbalance is lower than said threshold, the search for the optimum rotor ends; if the unbalance is lower than the optimum unbalance, the determination is made of the optimum rotor and of the optimum unbalance and of the existence of a possible permutation, it being understood that if the unbalance is lower than the optimum unbalance the system passes directly to the step of determination of a possible permutation, the search ending if no permutation is possible, whereas if a permutation is possible the system carrying out the permutation, calculating the unbalance of the rotor and then returning to the step of testing to know if the unbalance is lower than a predetermined threshold for a new sequence.

7. Device for pretreating via centrifuging samples contained in tubes placed in containers prior to being introduced into an automatic analysis device, the centrifuging being effected in a centrifugal machine comprising a rotor with a vertical axis, a plurality of boats being mounted tilting at the periphery of said rotor, said boats being able to each contain one container with tubes of samples said device comprising a feeding station placed along one lateral side of the centrifugal machine opposite a feeding station of the analysis robot, this feeding station comprising a first thrustor able to move in translation and used to extract the containers contained in the feeding station, bring them into a storage area adjacent to a belt conveyor which circulates parallel to the rear side of the centrifugal machine perpendicular to the displacement axis of the thrustor, a grasping mechanism able to transfer the containers situated on the belt conveyor into the boats of the centrifugal machine which come out of an opening situated in a feeding area and bring them back onto the belt conveyor after centrifuging, said belt conveyor transporting the centrifugal thrusters to a transport area situated on one lateral side of the centrifugal machine adjacent to the feeding station of the robot, said transport area comprising a second thrustor able to move perpendicular to the running off direction of the belt conveyor so as to transfer via a translation movement the containers brought by the belt conveyor into the feeding station of the robot.

8. Device according to claim 7, wherein the distribution of the containers in the feeding station of the robot is effected by means of an endless belt mounted on rollers axed vertically and bearing a drive cam.

9. Device according to claim 7 comprising a device for detecting the presence of tubes inside the containers at the time they move from the feeding station to the belt conveyor, this detection device comprising a row of detection jacks axed perpendicular to the displacement axis of the containers and mounted on a structure able to move in translation above the containers from the station to the belt conveyor.

10. Device according to claim 9, wherein said mobile structure of the device is integral with the structure of said grasping device.

* * * * *